United States Patent [19]

McKenna

[11] 4,423,600

[45] Jan. 3, 1984

[54] METHOD FOR PRESERVATION OF LIVING ORGANIC TISSUE BY FREEZING

[76] Inventor: Joan J. McKenna, 2811 Grove St., Berkeley, Calif. 94703

[21] Appl. No.: 448,467

[22] Filed: Dec. 10, 1982

[51] Int. Cl.³ ............................................. F25D 25/00
[52] U.S. Cl. ........................................... 62/62; 62/78; 62/100; 426/419; 426/524
[58] Field of Search ................... 62/100, 78, 268, 62; 426/419, 524

[56] References Cited

U.S. PATENT DOCUMENTS

| | | | |
|---|---|---|---|
| 1,422,627 | 7/1922 | Shaw . | |
| 2,304,192 | 12/1942 | Newton | 62/268 |
| 2,502,527 | 4/1950 | McFarlan | 62/104 |
| 2,786,342 | 3/1957 | Goetz | 62/62 |
| 2,832,690 | 4/1958 | Brunsing et al. | 99/193 |
| 3,077,036 | 2/1963 | Neumann | 62/100 |
| 3,180,738 | 4/1965 | Lassen | 62/78 |
| 3,219,463 | 11/1965 | Lamb | 99/204 |
| 4,054,672 | 10/1977 | Inoue et al. | 426/244 |
| 4,252,001 | 2/1981 | Musschoot | 62/268 |

*Primary Examiner*—Ronald C. Capossela
*Attorney, Agent, or Firm*—Townsend and Townsend

[57] ABSTRACT

A process for the freezing of organic tissue is disclosed, in which the atmospheric pressure in contact with the tissue is gradually lowered before or during the freezing process. The decompression is done at a rate and to a degree whereby a substantial portion of the gaseous matter dissolved in the cellular fluid is released to the atmosphere, without substantial vaporization of the fluid itself. The release of the dissolved gases permits freezing of the tissue without damage to the cellular structure, and thus permits a full return to the original appearance and consistency upon thawing.

11 Claims, No Drawings

METHOD FOR PRESERVATION OF LIVING ORGANIC TISSUE BY FREEZING

BACKGROUND OF THE INVENTION

1. Field of the Invention

This invention relates to the freezing and preservation of fruits, vegetables, animal matter and organic tissue in general. In particular, this invention relates to the freezing of cellular formations for purposes of storage, transportation, long-term preservation, and a variety of other uses where complete or partial suspension of biological activity is desired, with preservation or retention of the cell structure to afford a full return to the original condition upon reconstitution.

2. Description of the Prior Art

The freezing of fresh plants and living animal cells finds a wide range of utility, from the storage and transportation of fruits and vegetables for human consumption to the suspension of biological activity for facilitating surgical tissue repair or for medical or scientific observation. Unfortunately, most cell structures are unable to withstand the damage to the cell wall network caused by the formation of ice crystals, whose expanded volume and sharp edges cause puncturing of the cel walls and a bursting of the cells. The result is both a loss of tissue turgor and a loss of the natural juices. In the case of fruits and vegetables, the item may be edible after thawing, but it may no longer be palatable or attractive. In animal systems, severe metabolic disruption occurs, frequently resulting in death. In addition, air bubbles or emboli formed by trapped gases during freezing are released into the blood stream during thawing. Severe pain and immunological disruption can result, and an embolism in the heart or brain can cause death.

Known methods of overcoming this problem generally involve the partial dehydration of organic cells to provide room for the expansion which accompanies ice crystal formation. A typical process is disclosed by Lamb, U.S. Pat. No. 3,219,463 (Nov. 23, 1965). The Lamb process is a two-step procedure requiring a high level of vacuum (down to an absolute pressure of 4.6 torr). In order to reconstitute the material upon thawing, the boiled-off water must be replaced.

In complex or dense cellular structures, it is difficult to obtain an even distribution in this manner. Furthermore, tissues of delicate cell structure are often unable to withstand the stress accompanying a large amount of material passing through the cell walls during both dehydration and reconstitution.

SUMMARY OF THE INVENTION

It has now been discovered that the removal of at least a portion of the dissolved gases from the intracellular fluid of a cellular formation permits the freezing and reconstitution of the formation without substantial damage to the cell structure or the formation of emboli. The process of the invention thus provides a method of achieving full life suspension of a wide range of organic tissue, permitting a return to full viability upon thawing.

DESCRIPTION OF THE PREFERRED EMBODIMENTS

According to the process of the present invention, organic matter in the form of a cellular formation is subjected to gradual decompression and cooled to freezing or subfreezing temperature. Decompression is performed to the extent of substantially reducing the concentration of gases dissolved in the intracellular fluid, while avoiding substantial loss of the fluid itself by vaporization. The terms "gases" or "gaseous matter" are used herein to denote matter which is in the gaseous state under normal atmospheric conditions of temperature and pressure.

Reduction of the dissolved gas content produces a corresponding reduction of the increase in specific volume which occurs when the intracellular fluid is frozen. The present invention resides in the discovery that this reduction in frozen volume is sufficient to prevent the cell wall damage which otherwise accompanies the formation of ice crystals.

Decompression is performed at a rate which avoids fluid vaporization. The rate is otherwise not critical and can vary over a wide range. In general, a decompression rate falling within the range of about 1.0 to about 10.0 kilopascals per minute (7.1 to 77.0 torr per minute) will be most convenient. Preferred decompression rates are those falling within the range of about 3.0 to about 7.0 kilopascals per minute (23.0 to 53.6 torr per minute) with about 5.0 to about 6.0 kilopascals per minute (38.3 to 46.0 torr per minute) most preferred.

During decompression, the pressure is lowered to a point where a substantial quantity of the dissolved gas content is caused to escape from solution and pass through the cell walls, without causing a substantial amount of the cell fluid to evaporate. The actual level of decompression is not critical and can vary over a wide range, depending upon the type of organic tissue involved, the dissolved gas content, the cell wall structure and the nature of the cellular fluid. Preferably, at least about half of the dissolved gas content is released. With most organic materials, decompression to a level ranging from about 90 to about 60 kilopascals below atmospheric (70 to 300 torr absolute) will provide the best results. Within this range, a range of from about 80 to about 65 kilopascals below atmospheric (150 to about 260 torr absolute) is preferred.

The optimum decompression level varies not only with the type of organic matter, but with the altitude or climate in which the organic matter is grown. This is particularly true in the case of plant matter such as vegetables or fruits grown at high altitudes or in relatively cold or warm environments. The relatively fragile cell walls occurring in plants grown at high altitudes render the cell structure more susceptible to rupture and more permeable to the diffusion of gases and vapors. In such cases special care must be taken to avoid dehydration of the cells as well as to keep the cell structure intact. This can be accomplished by a reduction in the degree of decompression and the rate at which decompression occurs. Similar adjustments are frequently necessary for plants grown in cool or warm climates, due to variations in the quantity of dissolved gases present in the cellular fluids.

When particularly thick or strong cell walls are present, the cell response to decompression can be enhanced by a preliminary decompression-recompression cycle to temper the cell walls. The decompression and recompression portions of the cycle are both done at the rates indicated above, although a lesser pressure drop is used. Generally, effective tempering can be achieved by decompression to a pressure within the range of about 20 to about 40 kilopascals below atmospheric (450 to 600 torr absolute).

Decompression may be done either before or during the cooling process. Preferably, decompression and cooling are done simultaneously, to provide optimum control in permitting gases to escape while avoiding the loss of water. When done simultaneously, the relative rates of cooling and decompression must be such as to avoid flashing and yet avoid the formation of ice crystals before the gas is permitted to escape. Suitable rates are readily determined by routine experimentation. Upon thawing and reconstitution of the frozen material, those with a ruptured cell structure are readily determinable by their lack of turgor, whereas those which have suffered dehydration demonstrate a noticeable change in consistency and a partial loss of turgor. With the use of conventional cooling equipment and with decompression at the rates specified above, effective results are readily obtained, with the avoidance of both cell rupture and dehydration.

The ultimate temperature will be any temperature at which the intracellular fluids are frozen solid. This will vary with the nature of the solutes and the solute concentration, and thus with the type of organic tissue involved. In general, a temperature ranging from the normal freezing point of water to about $-10°$ C. will suffice.

Cooling can be accomplished by any conventional technique. When cooling and decompression are done simultaneously, it is necessary as stated above to moderate the cooling rate in order to permit the escape of gases from solution before substantial crystal formation can occur. Thus, flash freezing is preferably avoided.

In preferred practice of the process of the invention, cooling and decompression are accompanied by agitation and/or vibration of the cellular tissue, in order to promote the formation of masses of small ice crystals in the cell interiors, in preference over large crystals. Small crystals occupy a lesser volume, causing less distortion of the cell shape, and having fewer sharp edges or points capable of puncturing the cell walls. The rate and degree of agitation or vibration are not critical and can vary widely provided that small crystals are formed without causing abrasion or other damage to the cell structure, yet still permitting the escape of dissolved gases. Any device capable of inducing molecular movement within the tissue to an extent sufficient to disrupt or reorganize crystal formation can be used. This can range from gentle agitation to vibration at sonic frequency. The best results are achieved by a gentle agitation, continued at a steady rate until all the fluid in the cell structure is frozen solid. In most applications, a lateral oscillation at a rate of between about 25 and about 100 cycles per minute with a displacement amplitude of from about 1.0 to about 10.0 inches (2.5 to 25.0 cm) will provide the best results.

When dense or bulky materials are treated according to the process of the present invention, care should be taken to ensure that freezing occurs throughout the entire mass. Due to heat transfer limitations, inner portions, such as hearts of lettuce, crystallize more slowly than portions at or near the exterior cell layer. Thus, once the final temperature and decompression level are achieved, it is frequently necessary to maintain these conditions, as well as continuing the agitation when used, for a sufficient period of time to ensure complete freezing.

As a further option, moist or saturated air can be circulated around the object being frozen to provide a further means of preventing dehydration. Suitable circulating means are frequently incorporated into the construction of cooling devices. In any cases, cooling in an excessively dry environment should be avoided.

When live animals are placed in life suspension by freezing and decompression according to the process of the present invention, carbon dioxide or any other effective gaseous anesthetic may be used to minimize discomfort and facilitate restraint. The anesthetic will then be released during decompression, permitting the animal to fully recover upon thawing. In addition, the rapid cooling of tissues can be enhanced by the use of a helium-oxygen mixture to vent the cooling chamber.

Once the desired amount of dissolved gases has been permitted to escape and the tissues are completely frozen, the organic matter can be stored indefinitely in frozen condition, either at atmospheric pressure or under the partial vacuum under which the dissolved gases were released. The cell structure will remain intact provided that there is no thawing followed by refreezing.

When it is desired to return the organic material to its original condition, thawing is readily accomplished by a gradual warming of the material to ambient temperature. As the material is allowed to warm, the ice crystals within the cellular structure melt and atmospheric gases redissolve in the cellular fluid up to their equilibrium concentration.

The establishment of full turgor and return to the original condition may be enhanced by imposing a pressure upon the material in slight excess of atmospheric. This is particularly preferred when the organic matter consists of animal cells or whole animals in life suspension. In the most preferred practice, superatmospheric pressurization is done prior to thawing to reestablish intracellular pressure prior to return of the cell interiors to the fluid state.

The amount of excess pressure is not critical provided that it does not in itself cause damage to the cell structure. A pressure ranging from about 5% to about 10% above ambient pressure is sufficient for most applications. The rate of repressurization is likewise not critical, nor is it subject to the constraints necessary during decompression. Thus, a somewhat faster rate than that used for decompression is permissible, a typical such rate being within the range of about 5 to about 10 kilopascals per minute (38 to 77 torr per minute). Once complete thawing has occurred, the material can be returned to ambient temperature, whereupon excess gases within the cell walls will be released.

The process of the present invention is applicable toward the freezing and reviving of any vegetative or animal material, including fruits, vegetables, inedible plants, seeds, consumable meats, living cells and tissues, animal and human organs, whole animals and human beings. When vegetative material such as fruits or vegetables are used, best results are obtained when such materials are processed as soon as possible after harvesting. The process of this invention has utility in the improved storage and transportation of vegetative and animal matter, in the medical and scientific preservation and cells, tissues, organs and complex organisms, in the medical suspension of damaged or disintegrating tissues and organic systems for purposes of surgery or general medical care, and in the suspended animation of living cells and complex systems for biological preservation.

The following examples are offered for illustrative purposes and are intended neither to limit nor define the invention in any way.

EXAMPLE 1

Six standard laboratory mice and six heads of romaine lettuce were placed in an open 2.2 cubic foot (0.06 cubic meter) portable freezer set at −4° C., which in turn was placed inside a high altitude simulator with vibrational capacity. A vented high vacuum pump lowered the pressure in the simulator to that equivalent to an altitude of 37,000 feet (164 torr absolute or −78.2 kilopascals) at a steady rate over a period of about 20 minutes. During decompression, a lateral vibration was imposed on the system with a displacement of approximately three inches (7.6 cm) and a rate of 60 to 70 cycles per minute. Once the designated vacuum was achieved, the freezer was closed and vibration was continued for an hour and 45 minutes.

The vibration was then discontinued, the freezer re-opened and the pressure was permitted to return to atmospheric at a gradual rate over a 20-minute period. An additional 0.1 atmosphere pressure was then induced in the simulator to release the seals and facilitate the opening of the doors. The mice and lettuce were then removed.

The mice exhibited no vital signs and were stiff to the touch, clearly indicating that they were frozen. The mice were removed from their cages together with the cloths used to line the bottom of each cage. The mice and cloths were then placed in cardboard boxes for observation. Approximately 45 minutes after removal from the decompression chamber, one of the mice appeared to sigh. Within the next fifteen minutes, four of the remaining mice exhibited minor movements indicating a return of vital function. The sixth mouse exhibited movement approximately ten minutes later.

Water and food were supplied to all mice approximately one hour after removal from the decompression chamber. Throughout the next hour, all six mice appeared to remain in good health, exhibiting normal behavior and eating patterns.

The lettuce, upon removal from the vacuum chamber, was likewise stiff and completely frozen. The heads were placed on paper toweling to permit detection of any leakage due to cell rupture upon thawing.

Within fifteen minutes, the lettuce had significantly thawed and no leakage of cell contents was observed. Small areas which did not revive appeared near the edges of several of the leaves. This appeared to have been caused by bruising of the leaves prior to freezing. The main mass of the lettuce, however, revived with full turgor.

EXAMPLE 2

The apparatus used in Examples 2 through 6 consisted of a transparent vacuum chamber placed on a chemical agitator, all located inside a walk-in freezer. Decompression was achieved by use of a small vacuum pump, with pressure readings taken from a gauge atop the chamber.

A head of salad bowl lettuce was placed on an Ohaus scale inside the vacuum chamber, the scale indicating that the lettuce weighed 505 grams at the beginning of the experiment. The chamber was gradually decompressed to a vacuum of −77 kilopascals over a 20-minute period as the sample cooled, during which time the agitator was operating at approximately 50 cycles per minute with a lateral displacement of approximately three inches (7.6 cm). The freezer temperature was approximately −7° C. During decompression, the weight of the lettuce dropped by 10 grams ±2.

Once the desired vacuum level was reached, the conditions were maintained for an additional four hours. The vacuum chamber was then vented to gradually raise the pressure and return it to atmospheric. The recompression rate was 5 to 6 kilopascals per minute. The lettuce was then removed from both the vacuum chamber and the freezer and placed in the laboratory on paper toweling where it was permitted to thaw. The temperature in the laboratory was 68° F. (20° C.).

For purposes of comparison, two additional heads of the same variety of lettuce were similarly processed as controls. One of these, however, was simply placed in the freezer without either decompression or agitation and the other was decompressed and frozen without agitation. Otherwise the procedures were identical.

Within ten minutes of removal from the freezer, the first control sample (frozen without either decompression or agitation) exhibited staining of the toweling, indicating cell rupture and damage. The second control sample (frozen with decompression but without agitation) did not show staining of the towelling, but did exhibit a loss of turgor, appearing limp and resembling seaweed or kelp. The remaining sample (frozen with both decompression and agitation) maintained full turgor upon thawing and exhibited no fluid leakage. Again, a small section of one leaf did not revive, apparently due to a bruise and a small break in the capillaries serving the section.

EXAMPLE 3

Three heads of salad bowl lettuce were selected for experimentation, one having been picked from a garden the day of the experiment, and the others having been obtained from a produce seller at least four days after picking. All three heads were packed snugly into the decompression chamber of Example 2.

The heads were subjected to gradual decompression and agitation in the manner described in Example 2. After 45 minutes of agitation at the stabilized partial vacuum level, a visual inspection indicated that the heads were not completely frozen. Agitation at the low pressure was then continued for an additional 2 hours and 15 minutes, whereupon complete freezing was achieved.

Gradual recompression was then permitted to occur over a 20-minute period. All three heads were then removed from both the decompression chamber and the freezer and placed on paper toweling in the laboratory as described above. As the lettuce thawed, cell fluid leakage from the leaves which had been in contact with the side of the chamber was observed. Interior leaves did not exhibit leakage.

The head which had been picked the day of the experiment returned to full turgor. The heads which were four days from the field returned to only partial turgor.

EXAMPLE 4

A series of 4-inch (10.2 cm) pots each containing two living chrysanthemum plants with both open flowers and buds were placed in the decompression chamber and processed according to the procedure of Example 2. One plant in one pot had a stem slightly taller than the inner height of the chamber, and thus was in contact with the top of the chamber during freezing.

Final partial vacuum conditions were maintained with agitation for two hours, at which time the plants were recompressed and removed from both the chamber and the freezer to permit thawing in the laboratory. Within one hour, all plants were fully thawed. The leaves exhibited the same texture and turgor as they had prior to the experiment, although their color was slightly darker. The plants were then observed over a period of four weeks, and, with the exception of the stem that had been in contact with the chamber top, all continued to grow with blossoms intact and buds blossoming.

EXAMPLE 5

Four cherry tomatoes, three beefsteak tomatoes and two Italian tomatoes, all freshly picked, were placed in the decompression chamber of Example 2 and processed as described. In addition, two cherry tomatoes and two Italian tomatoes, also freshly picked, were placed on the agitator but outside the decompression chamber, for purposes of comparison. Finally, an endive which had been harvested 4 to 6 days earlier was also placed in the decompression chamber.

Final partial vacuum conditions were maintained with agitation for four hours due to the high water content of the tomatoes. The vegetables were then recompressed, removed from the chamber and freezer and placed in the laboratory on paper toweling to thaw.

Upon thawing, the control tomatoes (agitated but not decompressed) exhibited signs of cell rupturing and skin wrinkling and had a soft and pulpy consistency. The remaining tomatoes retained their original shape and firmness, with water droplets over the surface due to the sudden exposure to warm air. Several of the ripest tomatoes were darker in color than they were originally.

The endive upon thawing showed mixed response. Some leaves wilted without revival while others returned to full turgor.

EXAMPLE 6

Four heads of Mexican lettuce, including two romaine and two red leaf heads, which had been grown at an elevation of 2500 to 4000 feet (760 to 1220 meters) were processed as described in Example 2. Upon thawing of the heads, no cell rupture or fluid leakage was observed. Turgor was diminished, however, and the leaves had a rubber-like texture and a surface sheen not originally present.

An additional four heads of the same types of lettuce were processed similarly, except that decompression was done only to a level of −70 kilopascals (217 torr absolute), rather than −77 kilopascals. These heads upon thawing returned to full turgor, with texture and surface appearance identical to that exhibited before freezing.

The foregoing description is intended solely for purposes of illustration. The invention is not intended to be limited to the particular features or embodiments described. Numerous modifications and variations of the above still falling within the spirit and scope of the invention will be readily apparent to those skilled in the art.

What is claimed is:

1. A process for the freezing of organic tissue which comprises lowering the pressure of the atmosphere in contact with said tissue to release from said tissue at least a substantial portion of the gaseous matters dissolved therein with substantially no vaporization of water from said tissue, while cooling said tissue to a temperature at or below the freezing point thereof and agitating said tissue to disrupt crystal growth within said tissue.

2. A process according to claim 1 in which said agitation is performed at a rate of from about 25 to about 100 cycles per minute.

3. A process according to claim 1 in which the minimum pressure achieved is from about 90 to about 60 kilopascals below atmospheric.

4. A process according to claim 1 in which the minimum pressure achieved in step (a) is from about 80 to about 65 kilopascals below atmospheric.

5. A process according to claim 1 in which the rate at which said pressure is lowered is from about −3 to about −7 kilopascals per minute.

6. A process according to claim 1 in which the rate at which said pressure is lowered is from about −5 to about −6 kilopascals per minute.

7. A process according to claim 1 in which at least about half of the gaseous matter dissolved in said tissue is released.

8. A process according to claim 1 in which said organic tissue is vegetative matter and said process is conducted within about one day of harvesting.

9. A process for the freezing of organic tissue which comprises lowering the pressure of the atmosphere in contact with said tissue at a rate of from about −3 to about −7 kilopascals per minute to a minimum pressure of from about 90 to about 60 kilopascals below atmospheric to release from said tissue at least about half of the gaseous matter dissolved therein with substantially no vaporization of water from said tissue, while cooling said tissue to a temperature of from about −10° C. to about 0° C. and agitating said tissue at a rate of from about 25 to about 100 cycles per minute.

10. A process for the freezing of vegetative matter which comprises lowering the pressure of the atmosphere in contact with said matter at a rate of from about −5 to about −6 kilopascals per minute to a minimum pressure of from about 80 to about 65 kilopascals below atmospheric to release from said matter at least about half of the gaseous matter dissolved therein with substantially no vaporization of water from said vegetative matter, while cooling said vegetative matter to a temperature of from about −10° C. to about 0° C. and agitating said vegetative matter at a rate of from about 25 to about 100 cycles per minute, said process being conducted within about one day of harvesting said vegetative matter.

11. Frozen organic tissue prepared according to the process of claims 1, 2, 3, 4, 5, 6, 7, 8, 9, or 10.

* * * * *